United States Patent [19]

Israel et al.

[11] Patent Number: 6,127,178
[45] Date of Patent: Oct. 3, 2000

[54] APOPTOTIC PEPTIDES

[75] Inventors: Mark A. Israel, Belvedere; Monica Florio, San Francisco, both of Calif.

[73] Assignee: The Regents of the University of California, Oakland, Calif.

[21] Appl. No.: 09/045,764

[22] Filed: Mar. 20, 1998

[51] Int. Cl.[7] .............................. C12N 5/10; C12P 21/06; C12P 21/04; G01N 33/00; A01N 43/04
[52] U.S. Cl. .................. 435/375; 435/69.1; 435/69.7; 435/455; 436/86; 514/44
[58] Field of Search .................... 435/69.1, 69.2, 435/69.7, 325, 366, 372.1, 375, 455; 530/324; 436/86; 514/44

[56] References Cited

PUBLICATIONS

Verma et al. (Sep. 18, 1997) Nature, vol. 389, pp. 239–242.
Lasorella et al. (1996) Molecular and Cellular Biology, vol. 16, pp. 2570–2578.

Primary Examiner—Elizabeth Slobodyansky
Attorney, Agent, or Firm—Richard Aron Osman

[57] ABSTRACT

Apoptosis-promoting recombinant Id polypeptides comprise an Id N-terminus domainpeptides comprise an Id N-terminus domain peptide comprising an effective portion of the N-terminal domain of a natural Id protein. The polypeptides may be produced recombinantly from transformed host cells from the subject recombinant Id polypeptide encoding nucleic acids. The invention provides methods of making and using the subject compositions and mimic thereof to modulate cellular physiology, and especially promote apoptosis and in the biopharmaceutical industry.

22 Claims, 1 Drawing Sheet

```
MKVASGSAAAAAGPSCSLKAGRTAGEVVLGLSE  QSVAISR           CAGTRLPALL  DEQQVNVLLYDMNGCYSRLKELVPTLPQNRKVSKVEILQHVI DY
MKAFSPVR                           SVRKNSLSD HSLGISR              SKTPV  MSLLYNMNDCYSKLKELVPSIPQNKKVTKMEILQHVI DY
MKALSPVR                           GCYEAVCCLSE RSLAIAR            GRGKSPST EEP  LSILDDMNHCYSRLRELVPGVPRGTQLSQVEILQRVI DY
MKAVSPVR  PSGRKAPSGCGGGELALRCLAEHGHSLGGSAAAAAARCKAAEAAADEP  ALCLQCDMNDCYSRLRRLVPTIPPNRKVSKVEILQHVI DY
MKAISPVR           SMSSCYQAVCCLSE  QSLSIAR           GSSHKGPGM DEP  MGLLYDMNGCYSKLKELVPGIPQGSKLSQVEILQHVI DY
MKVVGPTC           ALKSSKVGGEDVVRCLSD QSLAISK        CKIPLL  DEQMTMFLQ  DMNSCYSKLKELVPTHPTNRKASKMEILQHVI DY
MKSLTAVC           QTGASGMPALNA    SGRIQRH           PTHRGDGENAEMKMYLSKLKDLVPFMPKNRKLTKLEIIQHVI DY

I RDLQLEL           NSESEVGTTGGRGL   PVRAPLSTLNGEISALAAEAACVP               ADDRILCR          SEQ ID NO:1
I LDLQIALDSHP       TIVSLHHQRPGQNQA  SRTRLTTLNTDISLSLQASEFP  SEL MSNDSKVLCG                    SEQ ID NO:2
I LDLQVVLAEPAPG     PPDGPHLPIQT                     AELTP  ELVISKDKRSFCH                       SEQ ID NO:3
I LDLQLALETHPALLRQPPPAPPLHPAGACPVAPPRTPLTALNTDP     AGAVNK           QGDSILCR                  SEQ ID NO:4
I FDLQIVLGEDQQQS                                    SILSLQKSDF  SEL ATQGDTSVCH  DDRIMCR        SEQ ID NO:5
I WDLQVELESKKNQTS                    APRTPLTTLN      AELASISVENGCS DDRIMCR                    SEQ ID NO:6
I CDLQTELETHPEMGNFDAAALTAVNGLHEDEDSDMEDADAEAEAEVDPDVLAQRLNAEQPAKVSSPAARLPL                     SEQ ID NO:7

TDRQTPNTLVAPAHPQQHQQQQLQLQQQQLQSQQQLSNSLATPQNAEKDSRQS                                          SEQ ID NO:7
```

FIG. 1

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 148 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Met Lys Val Ala Ser Gly Ser Ala Ala Ala Ala Ala Gly Pro Ser Cys
1               5                     10              15

```
Ser Leu Lys Ala Gly Arg Thr Ala Gly Glu Val Val Leu Gly Leu Ser
            20                  25                  30

Glu Gln Ser Val Ala Ile Ser Arg Cys Ala Gly Thr Arg Leu Pro Ala
            35                  40                  45

Leu Leu Asp Glu Gln Gln Val Asn Val Leu Leu Tyr Asp Met Asn Gly
            50                  55                  60

Cys Tyr Ser Arg Leu Lys Glu Leu Val Pro Thr Leu Pro Gln Asn Arg
65                  70                  75                  80

Lys Val Ser Lys Val Glu Ile Leu Gln His Val Ile Asp Tyr Ile Arg
            85                  90                  95

Asp Leu Gln Leu Glu Leu Asn Ser Glu Ser Glu Val Gly Thr Thr Gly
            100                 105                 110

Gly Arg Gly Leu Pro Val Arg Ala Pro Leu Ser Thr Leu Asn Gly Glu
            115                 120                 125

Ile Ser Ala Leu Ala Ala Glu Ala Ala Cys Val Pro Ala Asp Asp Arg
            130                 135                 140

Ile Leu Cys Arg
145
```

(2) INFORMATION FOR SEQ ID NO:2:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
            35                  40                  45

Leu Val Pro Ser Ile Pro Gln Asn Lys Lys Val Thr Lys Met Glu Ile
            50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
            85                  90                  95

Gln Ala Ser Arg Thr Arg Leu Thr Thr Leu Asn Thr Asp Ile Ser Ile
            100                 105                 110

Leu Ser Leu Gln Ala Ser Glu Phe Pro Ser Glu Leu Met Ser Asn Asp
            115                 120                 125

Ser Lys Val Leu Cys Gly
            130
```

(2) INFORMATION FOR SEQ ID NO:3:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Lys Ala Leu Ser Pro Val Arg Gly Cys Tyr Glu Ala Val Cys Cys
 1               5                  10                  15

Leu Ser Glu Arg Ser Leu Ala Ile Ala Arg Gly Arg Gly Lys Ser Pro
                20                  25                  30

Ser Thr Glu Glu Pro Leu Ser Leu Leu Asp Asp Met Asn His Cys Tyr
            35                  40                  45

Ser Arg Leu Arg Glu Leu Val Pro Gly Val Pro Arg Gly Thr Gln Leu
        50                  55                  60

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
                85                  90                  95

Leu Pro Ile Gln Thr Ala Glu Leu Thr Pro Glu Leu Val Ile Ser Lys
            100                 105                 110

Gln Lys Arg Ser Phe Cys His
            115
```

(2) INFORMATION FOR SEQ ID NO:4:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Lys Ala Val Ser Pro Val Arg Pro Ser Gly Arg Lys Ala Pro Ser
 1               5                  10                  15

Gly Cys Gly Gly Gly Glu Leu Ala Leu Arg Cys Leu Ala Glu His Gly
                20                  25                  30

His Ser Leu Gly Gly Ser Ala Ala Ala Ala Ala Ala Ala Ala Ala Ala
            35                  40                  45

Arg Cys Lys Ala Ala Glu Ala Ala Asp Glu Pro Ala Leu Cys Leu
        50                  55                  60

Gln Cys Asp Met Asn Asp Cys Tyr Ser Arg Leu Arg Arg Leu Val Pro
65                  70                  75                  80

Thr Ile Pro Pro Asn Lys Lys Val Ser Lys Val Glu Ile Leu Gln His
                85                  90                  95

Val Ile Asp Tyr Ile Leu Asp Leu Gln Leu Ala Leu Glu Thr His Pro
            100                 105                 110

Ala Leu Leu Arg Gln Pro Pro Pro Ala Pro Pro Leu His Pro Ala
        115                 120                 125

Gly Ala Cys Pro Val Ala Pro Pro Arg Thr Pro Leu Thr Ala Leu Asn
        130                 135                 140

Thr Asp Pro Ala Gly Ala Val Asn Lys Gln Gly Asp Ser Ile Leu Cys
145                 150                 155                 160

Arg
```

(2) INFORMATION FOR SEQ ID NO:5:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Lys Ala Ile Ser Pro Val Arg Ser Met Ser Cys Tyr Gln Ala
 1               5                  10                  15

Val Cys Cys Leu Ser Glu Gln Ser Leu Ser Ile Ala Arg Gly Ser Ser
                20                  25                  30

His Lys Gly Pro Gly Met Asp Glu Pro Met Gly Leu Leu Tyr Asp Met
            35                  40                  45

Asn Gly Cys Tyr Ser Lys Leu Lys Glu Leu Val Pro Gly Ile Pro Gln
    50                  55                  60

Gly Ser Lys Leu Ser Gln Val Glu Ile Leu Gln His Val Ile Asp Tyr
65                  70                  75                  80

Ile Phe Asp Leu Gln Ile Val Leu Gly Glu Asp Gln Gln Gln Ser Ser
                85                  90                  95

Ile Leu Ser Leu Gln Lys Ser Asp Phe Ser Glu Leu Ala Thr Gln Gly
                100                 105                 110

Asp Thr Ser Val Cys His
            115
```

(2) INFORMATION FOR SEQ ID NO:6:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Lys Val Val Gly Pro Thr Cys Ala Leu Lys Ser Ser Lys Val Gly
 1               5                  10                  15

Gly Glu Asp Val Val Arg Cys Leu Ser Asp Gln Ser Leu Ala Ile Ser
                20                  25                  30

Lys Cys Lys Ile Pro Leu Leu Asp Glu Gln Met Thr Met Phe Leu Gln
            35                  40                  45

Asp Met Asn Ser Cys Tyr Ser Lys Leu Lys Glu Leu Val Pro Thr His
    50                  55                  60

Pro Thr Asn Lys Lys Ala Ser Lys Met Glu Ile Leu Gln His Val Ile
65                  70                  75                  80

Asp Tyr Ile Trp Asp Leu Gln Val Glu Leu Glu Ser Lys Lys Asn Gln
                85                  90                  95

Thr Ser Ala Pro Arg Thr Pro Leu Thr Thr Leu Asn Ala Glu Leu Ala
                100                 105                 110

Ser Ile Ser Val Glu Asn Gly Cys Ser Asp Asp Arg Ile Met Cys Arg
            115                 120                 125
```

(2) INFORMATION FOR SEQ ID NO:7:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Lys Ser Leu Thr Ala Val Cys Gln Thr Gly Ala Ser Gly Met Pro
1               5                   10                  15

Ala Leu Asn Ala Ser Gly Arg Ile Gln Arg His Pro Thr His Arg Gly
            20                  25                  30

Asp Gly Glu Asn Ala Glu Met Lys Met Tyr Leu Ser Lys Leu Lys Asp
            35                  40                  45

Leu Val Pro Phe Met Pro Lys Asn Arg Lys Leu Thr Lys Leu Glu Ile
50                  55                  60

Ile Gln His Val Ile Asp Tyr Ile Cys Lys Leu Gln Thr Glu Leu Glu
65                  70                  75                  80

Thr His Pro Glu Met Gly Asn Phe Asp Ala Ala Ala Leu Thr Ala
                85                  90                  95

Val Asn Gly Leu His Glu Asp Glu Asp Ser Asp Met Glu Asp Ala Asp
            100                 105                 110

Ala Glu Ala Glu Ala Glu Val Asp Pro Asp Val Leu Ala Gln Arg Leu
            115                 120                 125

Asn Ala Glu Gln Pro Ala Lys Val Ser Ser Pro Ala Ala Arg Leu Pro
130                 135                 140

Leu Thr Asp Arg Gln Thr Pro Asn Thr Leu Val Ala Pro Ala His Pro
145                 150                 155                 160

Gln Gln His Gln Gln Gln Gln Leu Gln Leu Gln Gln Gln Gln Leu
                165                 170                 175

Gln Ser Gln Gln Gln Leu Ser Asn Ser Leu Ala Thr Pro Gln Asn Ala
            180                 185                 190

Glu Lys Asp Ser Arg Gln Ser
            195

(2) INFORMATION FOR SEQ ID NO:8:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
            35                  40                  45

Leu Val Pro Ser Ile Pro Gln Asn Lys Lys Val Ser Lys Met Glu Ile
50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
            85                  90                  95

Gln Ala Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
            115                 120                 125

Ser Lys Ala Leu Cys Gly
            130
```

(2) INFORMATION FOR SEQ ID NO:9:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Met Lys Ala Phe Ser Pro Val Arg Ser Val Arg Lys Asn Ser Leu Ser
 1               5                  10                  15

Asp His Ser Leu Gly Ile Ser Arg Ser Lys Thr Pro Val Asp Asp Pro
                20                  25                  30

Met Ser Leu Leu Tyr Asn Met Asn Asp Cys Tyr Ser Lys Leu Lys Glu
            35                  40                  45

Leu Val Pro Ser Ile Pro Gln Asn Lys Lys Val Thr Lys Met Glu Ile
50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Thr Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
        115                 120                 125

Ser Lys Val Leu Cys Gly
        130
```

(2) INFORMATION FOR SEQ ID NO:10:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Lys Ala Ile Ser Pro Val Arg Ser Phe Arg Lys Asn Ser Ser Asn
 1               5                  10                  15

Leu Ser Glu His Ser Leu Gly Ile Ser Arg Ser Lys Thr Pro Val Asp
                20                  25                  30

Asp Pro Leu Ser Leu Leu Tyr Asn Met Asn Asp Cys Tyr Ser Lys Leu
            35                  40                  45

Lys Glu Leu Val Pro Ser Ile Pro Gln Asn Lys Asn Val Ser Lys Met
50                  55                  60

Glu Ile Leu Gln His Val Ile Asp Tyr Ile Leu Asp Leu Gln Ile Ala
65                  70                  75                  80

Leu Asp Ser Asn Val Ala Ile Thr Ser His His Pro Arg Pro Gly
                85                  90                  95

Gln Ala Thr Pro Arg Thr Pro Leu Thr Thr Leu Asn Thr Asp Ile Ser
            100                 105                 110

Ile Leu Ser Leu Gln Ser Pro Glu Phe Pro Ser Asp Leu Ile Thr Asp
        115                 120                 125

Asp Ser Arg Thr Leu His Arg
        130                 135
```

(2) INFORMATION FOR SEQ ID NO:11:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Met Lys Ala Phe Ser Pro Val Arg Ser Val Arg Lys Asn Ser Leu Leu
 1               5                  10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
            35                  40                  45

Leu Val Pro Ser Ile Pro Gln Asn Lys Lys Val Ser Lys Met Glu Ile
        50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Leu Asn Thr Asp Ile Ser Ile Leu
                100                 105                 110

Ser Leu Gln Ala Ser Glu Phe Pro Ser Glu Leu Met Ser Asn Asp Ser
            115                 120                 125

Lys Ala Leu Cys Gly
        130
```

(2) INFORMATION FOR SEQ ID NO:12:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Met Lys Ala Phe Ser Pro Val Arg Ser Ile Arg Lys Asn Ser Leu Leu
 1               5                  10                  15

Asp His Arg Leu Gly Ile Ser Gln Ser Lys Thr Pro Val Asp Asp Leu
            20                  25                  30

Met Ser Leu Leu
            35
```

APOPTOTIC PEPTIDES

FIELD OF THE INVENTION

The field of this invention is polypeptides involved in cellular apoptosis.

BACKGROUND

The signals regulating apoptosis during the development of individual tissues are poorly understood, but a number of experimental systems has provided insights into the molecular mechanisms of several apoptotic pathways and the molecules which mediate them. Observations demonstrating that inappropriate entry into S phase is frequently associated with programmed cell death have been interpreted as indicating that these two cellular activities are coordinately regulated (3, 22, 43, 51, 73). Several genes which regulate cell-cycle progression also modulate apoptosis. Among these are the tumor suppressor proteins E2F-1, pRb, and p53 and oncoproteins such as E6, c-Jun, and c-Myc (3, 7, 22, 27, 31, 51, 55, 60, 66, 73). Evidence that the $G_1$ checkpoint regulator p53 can cooperate with E2F to augment apoptosis, and that c-Myc and E2F-1-induced apoptosis occurs when cells are deprived of mitogenic factors (3, 22, 30) supports a model in which activation of the cell death pathway is due to a conflict between growth-promoting and growth-inhibitory signals (31, 43, 51, 73). According to this view, the tendency of cells to undergo apoptosis when receiving divergent growth signals may result from a dysregulated expression of cell cycle modulators and the unscheduled activation of their target genes.

Recent observations, however, have challenged this model by demonstrating that dual regulators of proliferation and apoptosis promote these processes by separate mechanisms (71). Active $G_1$ cyclin/Cdk complexes are necessary for proliferation but not apoptosis mediated by c-Myc. Also, c-Myc-induced cell cycle progression and apoptosis can be separated pharmacologically (54, 64). More recently it has been demonstrated that the ability of E2F-1 to transactivate genes required for progression into S-phase can be uncoupled from its ability to activate apoptosis (9, 33, 58). Similar observations have been reported for the p53 tumor suppressor whose ability to induce growth arrest and apoptosis are genetically separable (9). These findings support the notion that, while several regulators of the cell death and growth pathways are shared, their functional activities in these pathways are distinct. How these divergent activities are coordinated remains unknown.

Id proteins comprise a family of helix-loop-helix (/BLH) transcription factors that are important regulators of cellular differentiation and proliferation (5, 6, 11, 21, 61, 69, 75). Id proteins lack a basic DNA binding region and are capable of inhibiting gene expression by forming inactive heterodimers with bHLH transcription factors, thereby blocking the binding of bHLH factors to specific DNA sequences, E-boxes, found in the regulatory regions of their target genes (11, 40, 48, 52, 56, 69). During cellular proliferation and prior to the onset of differentiation, Id genes are typically expressed at high levels (5, 19, 35, 36, 42, 69) and enforced overexpression of Id genes inhibits differentiation of a variety of cell lineages (13, 18, 38, 42, 47, 50, 67, 68). In addition, constitutive expression of Id1 in B-cells of transgenic mice inhibits B-cell maturation during the establishment of the immune system (68).

Id gene expression is enhanced in response to mitogenic stimuli (4, 5, 11, 16) and has been implicated in the induction of DNA synthesis (57). Ectopic expression of Id1 or Id2 enhances proliferation of several cell types (34, 59). Furthermore, treatment of cells with antisense Id1 oligonucleotides or microinjection of Id1 neutralizing antibodies prevents re-entry of serum deprived cells into the cell-cycle (4, 28). Some aspects of the mechanisms by which Id proteins enhance proliferation have been described: Id2 binds to the unphosphorylated retinoblastoma protein (pRb) family members and abolishes their growth-suppressing function (34, 45), and Id1a inhibits expression of p21/WAF1, an inhibitor of cyclin dependent kinases (59). Moreover, Id2 can antagonize the growth inhibition of several tumor suppressor proteins whose action is mediated by pRb including p21 and p16 (45). Other components of the cell cycle machinery interact with Id2 as well. Recently, Id2 was shown to be an in vivo substrate of the $G_1$-cyclin-dependent kinases, cyclin A- and cyclin E/Cdk2 (29). The only other substrates identified for these kinases are the Rb family of tumor suppressors, pRb, p107 and p130, and certain E2F family members, all of which are important for the $G_O$ to S-phase transition (for a review see 72).

We have found that intracellular overexpression of Id2 N-terminal domain containing polypeptides can modulate apoptosis. To date, all Id protein functions have been ascribed to the HLH sequence motif, which mediates heterodimerization with b/HLH transcription factors (5) and the association of Id2 with Rb family members (34, 45). Furthermore, the ability of certain bHLH transcription factors to induce apoptosis has been assigned exclusively to their HLH//LZ dimerization domains (Kohluber et al., 1995, J.Biol.Chem. 270, 28797–28805). Strikingly, Id2 transmits an apoptotic death signal that is independent of its ability to dimerize with bHLH members. Since the Id2 HLH domain is required for interactions with the pRB family (34, 45), the cell death and growth promoting activities of Id2 are separable. We found that the apoptotic activity of the N-terminal region of Id2 is associated with the expression of a known modulator of the programmed cell death cascade, Bax, indicating a role for Id2 in integrating the divergent cellular activities of growth and apoptosis.

Cited Literature

1. Almasan, A., et al. 1995. Proc. Natl. Acad. Sci. 92: 5436–5440.
2. Andres-Barquin P. J., et al. 1997. Cancer Res. 57: 215–220.
3. Askew, D. S., et al. 1991. Oncogene 6: 1915–1922.
4. Barone, M. V., et al. 1994. Proc. Natl. Acad. Sci. 91: 4985–4988.
5. Benezra, R., et al. 1990. Cell 61: 40–61.
6. Biggs, J. R., et al. 1992. Proc. Natl. Acad. Sci. 89: 1512–1516.
7. Bossy-Wetzel E., L. Bakiri, and M. Yaniv. 1997. EMBO J. 16: 1695–1709.
8. Chen, B., et al. 1997. Nucleic Acids Res. 25: 423–430.
9. Chen, X, et al.. 1996. Genes & Dev. 10: 2438–2451.
11. Christy, B. A, et al. 1991. Proc. Natl. Acad. Sci. 88: 1815–1819.
12. Cleveland, J. L., et al. 1994. Oncogene 9: 2217–2226.
13. Cordle, S. R., et al. 1991. Mol. Cell. Biol. 11: 1734–1738.
14. Condorelli, G. L., et al. 1997. Mol. Cell. Biol. 17: 2954–2969.
15. Cubas, P., et al. 1994.. Development 120: 2555–2566.
16. Deed, R. W., et al. 1993. Oncogene 8: 599–607.
17. Deed, R. W., et al. 1996. J. Biol. Chem. 271:23603–23606.
18. Desprez, P. Y., et al. 1995. Mol. Cell. Biol. 15:3398–3404.

19. Einarson M. B. and M. V. Chao. 1995. Mol. Cell. Biol. 15:4175–4183.
20. Ellis, H. M., D. R. Spann, D. R. and J. W. Posakony. 1990. Cell 61:27–38.
21. Ellmeier, W., et al. 1992. EMBO J. 11:2563–2571.
22. Evan, G. I., et al. 1992. Cell 69:119–128.
23. Fanidi, A., E. A. Harrington, and G. I. Evan. 1992. Nature 359:554–556.
24. Garrell, J. and J. Modolell. 1990. Cell 61:39–48.
25. Gavrieli Y., et al.. 1992. J. Cell Biol. 119:493–501.
26. Gossen, M., et al. 1995. Science 268:1766–1769.
27. Haas-Kogan, D., et al. 1995. EMBO J. 14:461–472.
28. Hara, E., et al. 1994. Biol. Chem. 269:2139–2145.
29. Hara, E., M. Hall, and G. Peters. 1997. EMBO J. 16:332–342.
30. Harrington, E. A., et al. 1994. EMBO J. 13:3286–3295.
31. Hiebert, S. W., et al. 1995. Mol. Cell Biol. 15:6864–6874.
32. Hinds P. W. and R. A. Weinberg. 1994. Curr. Opin. Genet. Devel. 4:135–141.
33. Hsieh J. K., et al. 1997. Genes & Dev. 11:1840–1852.
34. Iavarone, A., et al. 1994. Genes & Dev. 8:1270–1284.
35. Ishiguro, A., et al.. 1996.. Blood 87:5225–5231.
36. Ishiguro, A., et al. 1995. Leuk. Res. 19:989–996.
37. Jen, Y., K. Manova, and R. Benezra. 1996. Dev. Dynam. 207: 235–252.
38. Jen, Y., H. Weintraub, and R. Benezra. 1992. Genes & Dev. 6: 1466–1479.
39. Jen, Y., K. Manova, and R. Benezra. 1997. Dev. Dynam. 208:92–106.
40. Kadesch, T. 1993. Cell Growth Differ. 4:49–55.
41. Kowalik, T. F., et al. 1995. J. Virol. 69:2491–2500.
42. Kreider, B., et al. 1992. Science 255:1700–1702.
43. Krek, W., G. Xu, and D. Livingston. 1995. Cell 83:1149–1158.
44. Kurabayashi M., R. Jeyaseelan, and L. Kedes. 1993. Gene 133:305–306.
45. Lasorella, A., et al.. 1996. Mol. Cell. Biol. 16:2570–2578.
46. Le Jossic C., et al. 1994. Cancer Res. 54: 6065–6068.
47. Lister, J., et al. 1995. J. Biol. Chem. 270:17939–17946.
48. Littlewood, T. D. and G. I. Evan. 1995. Protein Profile 2:621–702.
49. McLeod, K. F., Y. Hu, and T. Jacks. 1996. EMBO J. 15:6178–6188.
50. Moldes, M., et al. 1997. Mol. Cell. Biol. 17:1796–1804.
51. Morgenbesser, S. D., et al. 1994. Nature 371:72–74.
52. Murre, C., P. S. McCaw, and D. Baltimore. 1989. Cell 56: 777–783.
53. Nicoletti, I., et al. 1991. J. Immunol. Methods 139:271–279.
54. Packham, G., C. Porter, and J. L. Cleveland. 1996. Oncogene 13:461–469.
55. Pan, H. and A. E. Griep. 1994. Genes & Dev. 8:1285–1299.
56. Pesce, S. and R. Benezra. 1993. Mol. Cell. Biol. 13:7874–7880.
57. Peverali, F. A., et al. 1994. EMBO J. 13:4291–4301.
58. Phillips, A. C., et al. 1997. Genes & Dev. 11:1853–1863.
59. Prabhu, S., et al. 1997. Mol. Cell. Biol. 17:5888–5895.
60. Qin, X. Q., et al. 1994. Proc. Natl. Acad. Sci. 91:10918–10922.
61. Riechmann, V., et al. 1994. Nucleic Acids Res. 22:749–755.
62. Rodriguez-Tarduchy, G. M., et al.. 1990. EMBO J. 9:2997–3002.
63. Rowan, S., et al. 1996. EMBO J. 15:827–838.
64. Rudolph, B., et al. 1996. EMBO J. 15:3065–3076.
65. Schmitz, G. G., et al. 1991.. Anal. Biochem. 192:222–231.
66. Shan, B. and W. H. Lee. 1994. Mol. Cell. Biol. 14:8166–8173.
67. Shoji, W., et al. 1994. J. Biol. Chem. 269:5078–5084.
68 . Sun X. -H. 1994. Cell 79:893–900.
69. Sun, X. -H., et al. 1991. Mol. Cell. Biol. 11:5603–5611.
70. Steller, H. 1995. Science 267:1445–1449.
71. Wagner, A. J., et al. 1994. Genes & Dev. 8:2817–2830.
72. Weinberg, R. A. 1995. Cell 81:323:330.
73. Wu, X. W. and A. J. Levine. 1994. Proc. Natl. Acad. Sci. 91:3602–3606.
74. Zacksenhaus, E., et al. 1996. Genes & Dev. 10:3051–3064.
75. Zhu W., et al.. 1995. Molecular Brain Research 30:312–326.

SUMMARY OF THE INVENTION

The invention provides methods and compositions for regulating, e.g. promoting or inhibiting, apoptosis of a cell. The general methods comprise the steps of introducing into the cell a nucleic acid encoding a polypeptide comprising the N-terminal 35 residues of a natural Id protein, or an apoptosis-modulating peptide thereof, under conditions whereby the nucleic acid is expressed in the cell and apoptosis of the cell is modulated, and preferably, confirming the modulation of apoptosis of the cell. For example, the polypeptide may comprise at least one of a first peptide comprising at least the N-terminal 8 residues of a natural Id protein, and a second peptide comprising at least 12 other non-overlapping consecutive residues of the N-terminal 35 residues of a natural Id protein, or a mimic thereof. The nucleic acid may be introduced by, for example, transfecting the cell or an ancestor of the cell with the nucleic acid, by upregulating the expression of a resident nucleic acid, such as a stably or transiently transfected gene, etc.

The general method for inhibiting apoptosis in a cell comprises the step of introducing into the cell an antagonist of an apoptosis-promoting N-terminus peptide of an endogenous Id protein. For example, the antagonist may be a nucleic acid which inhibits the expression of a native Id protein, generally by hybridizing with, and inhibiting translation of, a transcript of the gene encoding the native Id protein. Such inhibitory nucleic acids comprise anti-sense sequences of resident Id transcripts sufficient to effect specific, intracellular hybridization thereto.

The subject methods may be practiced in vitro or in vivo. Preferred in vivo applications effect the selective death of target cells, particularly preferentially susceptible tumor cells. In vitro applications include cell-based drug screens for agents which antagonize or mimic the effects of the subject peptides. A particular screen comprises the steps of introducing into the cell a nucleic acid encoding a subject polypeptide or mimic, under conditions whereby the nucleic acid is expressed in the cell and apoptosis of the cell is promoted, contacting the cell with an agent, and determining whether the agent modulates the promotion of apoptosis in the cell.

BRIEF DESCRIPTION OF THE DRAWING

FIG. 1 is an alignment of exemplary Id proteins—murine sequences from Id1 (SEQ ID NO: 1), Id2 (SEQ ID NO:2), Id3 (SEQ ID NO:3), Id4 (SEQ ID NO:4), Xenopus (Xidx—SEQ ID NO:5), Zebrafish (Zid—SEQ ID NO:6) and Drosophila (emc—SEQ ID NO:7)—, showing N-terminal, HLH and C-terminal domains.

DETAILED DESCRIPTION OF PARTICULAR EMBODIMENTS OF THE INVENTION

The invention provides methods and compositions relating to N-terminal domains of Id proteins, which compositions find a wide variety of uses including use as immunogens, targets in screening assays, bioactive reagents for modulating cell growth, differentiation and/or function, etc.

In one embodiment, the invention provides methods for promoting apoptosis of a cell, comprising the step of introducing into the cell a nucleic acid encoding a polypeptide comprising an effective portion of the N-terminal domain of a natural Id protein, under conditions whereby the nucleic acid is expressed in the cell and apoptosis of the cell is promoted. Id protein N-terminal, HLH and C-terminal domains and their boundaries are well-established in the art and clearly discernable from alignments of Id proteins, e.g. see FIG. 1. In particular, the HLH domain comprises a highly conserved 15:7:19 residue helix:loop:helix domain. Effective (i.e. sufficient to effect apoptotic modulation as described below) N-terminal portions are readily derived empirically, in rapid and convenient assays, as described below. In a particular embodiment, the polypeptides comprise at least one of first and second Id peptides, wherein the first peptide comprises residues 1–8 of at least one of SEQ ID NOS:01–12 and the second peptide comprises least one of residues 27–40 of SEQ ID NO:1; residues 11–24 of SEQ ID NO:2; residues 13–26 of SEQ ID NO:3; residues 24–37 of SEQ ID NO:4; residues 16–29 of SEQ ID NO:5; residues 20–33 of SEQ ID NO:6; residues 14–27 of SEQ ID NO:7; residues 11–24 of SEQ ID NO:8; residues 11–24 of SEQ ID NO:9; residues 11–24 of SEQ ID NO:10; residues 11–24 of SEQ ID NO:11; and residues 11–24 of SEQ ID NO:12.

In other embodiments, the polypeptide comprises at least 25, preferably at least 30 consecutive residues of the N-terminal 35 residues of a natural Id protein, and more preferably the entire, or essentially the entire Id domain N-terminal to the HLH domain. The N-terminal sequences derive from natural Id genes, preferably human Id genes, more preferably human Id2 genes. The polypeptides do not have a functional Id HLH domain, e.g. the corresponding HLH domain may be entirely or partially omitted/deleted or mutated. A wide variety of mutations, including deletions, insertions and substitutions within the HLH domain are found to inactivate the HLH domain, as determined by convenient dimerization assays. Preferred polypeptides do not have an intact native Id C-terminal domain. In yet another embodiment, the polypeptide comprises fewer than 30, preferably fewer than 20, more preferably fewer than 10 consecutive residues of the C-terminal 35 residues of a natural Id protein. Exemplary recombinant apoptotic Id polypeptides are shown in Table 1.

TABLE 1

Exemplary effective Id polypeptides (asterisked mutants are expressed as recombinant fusions with a yeast signal sequence).

| Mutant | Sequence | Induced Apoptosis |
|---|---|---|
| Am1Id1-1* | SEQ ID NO:1, residues 1–8 | + |
| AmId2-1* | SEQ ID NO:2, residues 1–8 | + |
| AmId3-1* | SEQ ID NO:3, residues 1–8 | + |
| AmId4-1* | SEQ ID NO:4, residues 1–8 | + |
| AxId-1* | SEQ ID NO:5, residues 1–8 | + |
| AzId-1* | SEQ ID NO:6, residues 1–8 | + |
| AdId-1* | SEQ ID NO:7, residues 1–8 | + |
| AhId2-1* | SEQ ID NO:8, residues 1–8 | + |
| ArId2-1* | SEQ ID NO:9, residues 1–8 | + |
| AtId-1 * | SEQ ID NO:10, residues 1–8 | + |
| Am1Id-1* | SEQ ID NO:11, residues 1–8 | + |
| Am3Id2-1* | SEQ ID NO:12, residues 1–8 | + |
| Am1Id1-2 | SEQ ID NO:1, residues 27–40 | + |
| AmId2-2 | SEQ ID NO:2, residues 11–24 | + |
| AmId3-2 | SEQ ID NO:3, residues 13–26 | + |
| AmId4-2 | SEQ ID NO:4, residues 24–37 | + |
| AxId-2 | SEQ ID NO:5, residues 16–29 | + |
| AzId-2 | SEQ ID NO:6, residues 20–33 | + |
| AdId-2 | SEQ ID NO:7, residues 14–27 | + |
| AhId2-2 | SEQ ID NO:8, residues 11–24 | + |
| ArId2-2 | SEQ ID NO:9, residues 11–24 | + |
| AtId-2 | SEQ ID NO:10, residues 11–24 | + |
| Am1Id-2 | SEQ ID NO:11, residues 11–24 | + |
| Am3Id2-2 | SEQ ID NO:12, residues 11–24 | + |
| AhId2-3 | SEQ ID NO:8, residues 1–7 and 70–134 | + |
| AhId2-4 | SEQ ID NO:8, residues 11–24 and 77–134 | + |
| AhId2-5 | SEQ ID NO;8, residues 2–35 | + |
| AhId2-6 | SEQ ID NO:8, residues 1–8 and 11–24 | + |
| AhId2-7 | SEQ ID NO:8, residues 1–8 and 14–29 | + |
| AhId2-8 | SEQ ID NO:8, residues 1–35 and 44–134 | + |

The polypeptide may comprise a wide variety of other components or be incorporated in a larger complex. For example, the polypeptide may include additional Id or non-Id peptide sequence(s) which enhance the protein's stability, provide selective targeting, etc., e.g. yeast specific signal sequences. Additionally, the polypeptide may be incorporated into a glycoprotein, riboprotein, etc. A wide variety of molecular and biochemical methods are available for biochemical synthesis and molecular expression of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art.

A wide variety of methods may be used to introduce the subject peptides into a target cell, generally by effecting the expression within the cell of a nucleic acid encoding the subject polypeptide. Nucleic acids encoding the subject peptides may be derived from native Id gene or transcript sequences, which may be further modified, recombined, etc. for particular expression designs. Alternatively, the amino acid sequences of the subject polypeptides are used to back-translate apoptotic Id domain polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural Id-encoding nucleic acid sequences ("GCG" software, Genetics Computer Group, Inc, Madison, Wis.).

Cellular expression may be effected by transfecting the cell or an ancestor of the cell with the nucleic acid, by upregulating the expression of a resident nucleic acid such as a transgene encoding the subject polypeptide, etc. A wide variety of techniques for introducing the nucleic acids into viable cells and making transgenic animals are known and well-established in the art and include retroviral-based transfection, viral coat protein-liposome mediated transfection, cloning techniques, etc. For example, the subject apoptotic Id polypeptides are readily introduced into immuno-compromised animals bearing susceptible human tumors (e.g. osteocarcinomas) by several well-established methodologies, including the adenovirus gene delivery systems described by Wilson (1996) New Engl. J. Med. 334, 1185–1187 and Badie et al. (1998) J. Neuro-Oncology37:217–222, and shown to promote selective apoptosis of the targeted tumor cells. Alternatively, in vivo efficacy is similarly demostrated by expressing the subject polypeptides using a tetracycline-regulated system providing autoregulatory inducible apoptotic Id gene expression in transgenic animals according to the methods described in Shockett et al (1995) Proc.Natl.Acad.Sci.USA 92, 6422–6526. An alternative animal system for demonstrating in vivo efficacy involves expressing the Id peptides under the control of a tetracycline-responsive promoter is produced as described by Furth (1994) Proc.Natl.Acad.Sci.USA 91, 9302–9306.

A wide variety of target cells are susceptible to the subject methods. Cells susceptible to apoptotic induction are readily identified emprically, in in vitro or cell- or animal-based screens, as described in the examples below. In a preferred embodiment, the target cells are preferentially susceptible cancer cells. Similarly, and as exemplified below, a wide variety of methods well known in the art confirming the modulation of apoptosis of a target cell.

Id protein inhibitory nucleic acids are typically antisense: single-stranded sequences comprising complements of the disclosed natural Id apoptotic peptide domain coding sequences. Antisense modulation of the expression of a given apoptotic Id peptide may employ antisense nucleic acids operably linked to gene regulatory sequences. In this embodiment, cells are transfected with a vector comprising an apoptotic Id peptide sequence with a promoter sequence oriented such that transcription of the gene yields an antisense transcript capable of binding to endogenous apoptotic Id peptide encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given apoptotic Id peptide may be administered to the target cell, in or temporarily isolated from a host, at a concentration that results in a substantial reduction in expression of the targeted protein.

The invention also provides binding agents specific to the subject polypeptides, methods of identifying and making such agents, and their use in diagnosis, therapy and pharmaceutical development. These binding agents necessarily distinguish native Id proteins comprising functional HLH domains. For example, specific binding agents are useful in a variety of diagnostic and therapeutic applications, especially where disease or disease prognosis is associated with improper utilization of a pathway involving apoptotic Id domains. Novel Id N-terminal-specific binding agents include Id N-terminal-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural binding agents such as Id N-terminal intracellular binding targets or receptors, non-natural intracellular binding agents identified in screens of chemical libraries such as described below, etc.

The invention provides efficient methods of identifying agents, compounds or lead compounds for agents active at the level of an apoptotic Id peptide modulatable cellular function. Generally, these screening methods involve assaying for compounds which modulate apoptotic Id peptide interaction with a natural apoptotic Id peptide binding target. A wide variety of assays for binding agents is provided including labeled in vitro protein-protein binding assays, immunoassays, cell based assays, gel shift assays (e.g. Kreider, B., R. Benezra, G. Rovera, and T. Kadesch. 1992. Science 255:1700–1702), etc. The methods are amenable to automated, cost-effective high throuphput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an apoptotic Id peptide, which may be part of a fusion product with another peptide or polypeptide, e.g. a tag for detection or anchoring, etc. The assay mixtures comprise a natural intracellular apoptotic Id peptide binding target protein. While native binding targets may be used, it is frequently preferred to use portions thereof so long as the portion provides binding affinity and avidity to the subject apoptotic Id peptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents such as salts, buffers, neutral proteins, e.g. albumin, detergents, protease inhibitors, nuclease inhibitors, antimicrobial agents, etc. may also be included. The mixture components can be added in any order that provides for the requisite bindings and incubations may be performed at any temperature which facilitates optimal binding. The mixture is incubated under conditions whereby, but for the presence of the candidate pharmacological agent, the apoptotic Id peptide specifically binds the intracellular binding target, portion or analog with a reference binding affinity. Incubation periods are chosen for optimal binding but also minimized to facilitate rapid, high-throughput screening.

After incubation, the agent-biased binding between the apoptotic Id peptide and one or more binding targets is detected by any convenient way. For cell-free binding type assays, a separation step is often used to separate bound from unbound components. Separation may be effected by precipitation, immobilization, etc., followed by washing by, for example, membrane filtration, gel chromatography. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the apoptotic Id peptide to the target in the absence of the agent as compared with the binding affinity in the presence of the agent indicates that the agent modulates the binding of the apoptotic Id peptide to the corresponding binding target. A difference, as used herein, is statistically significant and preferably represents at least a 50%, more preferably at least a 90% difference.

Another method for generating agents active at the level of an apoptotic Id peptide modulatable cellular function involves making mimics of the subject apoptotic Id peptides. Such mimics may be substituted for the subject peptides and/or polypeptides in the foregoing methods for modulating apoptosis of a cell, i.e. comprising the steps of generating a mimic of an apoptosis modulating peptide of the N-terminal 35 residues of a natural Id protein, preferably of at least one of a first peptide comprising at least the N-terminal 8 residues of a natural Id protein and a second peptide comprising at least 12 other nonoverlapping consecutive residues of the N-terminal 35 residues of a natural Id protein, wherein the peptide, when expressed in a susceptible cell, is capable of modulating apoptosis of the cell; introducing the mimic into the cell, under conditions whereby the mimic modulates apoptosis of the cell; and, preferably confirming the modulation of apoptosis of the cell. Methods for generating a wide variety of mimics to defined peptides are well known in the art. See e.g. Fairlie D P, et al. (1998) Curr Med Chem 5(1):29–62 and Konings D A, et al. (1997) J Med Chem 40(26):4386–4395. Specific methodologies for generating mimics of apoptotic Id peptides are described, inter alia, in LeSauteur L, et al. (1995) J Biol Chem 270(12):6564–6569; Baures P W, et al. (1997) J Med Chem 40(22):3594–3600; Chen S, et al. (1997) J Med Chem 40(23):3842–3850; Monfardini C, et al. (1996) J Biol Chem 271(6):2966–2971 and Webber S E et al. (1996) J Med Chem 39(26):5072–5082. Exemplary active mimics of apoptotic Id peptides are shown in Table 1.

TABLE 2

Exemplary active mimics of apoptotic hId2 peptides. Asterisked mutants are expressed as recombinant fusions with a yeast signal sequence. Substitutions are indicated in parentheses.

| Mimic | Sequence | Induced Apoptosis |
| --- | --- | --- |
| ΔhId2-9* | SEQ ID NO:8, residues 1–8 (Val7-Leu) | + |
| ΔhId2-10* | SEQ ID NO:8, residues 1–8 (Lys2-Arg) | + |
| ΔhId2-11 | SEQ ID NO:8, residues 1–8 (Ser5-Thr) | + |
| ΔhId2-12* | SEQ ID NO:8, residues 1–8 (Val7-Leu, Lys2-Arg) | + |
| ΔhId2-13* | SEQ ID NO:8, residues 1–8 (Val7-Leu, Ser5-Thr) | + |
| ΔhId2-14* | SEQ ID NO:8, residues 1–8 (Lys2-Arg, Ser5-Thr) | + |
| ΔhId2-15* | SEQ ID NO:8, residues 1–8 (Val7-Leu, Lys2-Arg, Ser5-Thr) | + |

The following examples are offered by way of illustration and not by way of limitation.

EXAMPLES cDNA constructs and establishment of cell lines. The mouse 32D.3 myeloid cell line was maintained in RPMI 1640 medium (GIBCO) supplemented with 10% fetal calf serum and 20U of IL-3 per ml as previously described (3, 12). The human IdI, Id2 and Id3 cDNAs (5, 6, 11) were introduced into the pMAM-Neo expression plasmid (Clontech, Palo Alto, Calif.) at the XhoI site. Mutations in Id2 and Id3 were generated by the polymerase chain reaction. To prepare an N-terminus deletion mutant, a 0.3 kb SalI-XhoI fragment lacking the region encoding amino acids 1–34 was inserted into the pMAM vector. A C-terminally truncated Id2 was prepared by removing a SmaI fragment containing cDNA corresponding to amino acids 93–135. Id2ΔHLH was prepared as previously described (34) and subcloned into the pMAM vector at the XhoI site. The primary structure of all mutants was confirmed by DNA sequencing. 32D.3 cells were electroporated as previously described with 10 μg of linearized plasmid DNA (12). Transfected cells were selected in medium containing 0.4/mg/ml G418 and single cell clones were isolated by limiting dilution, as well as pools of transfectants. To prepare additional cultures, drug-resistant clones and pools of clones were prepared by transfecting cells with pMAMNeo DNA alone and pMAMNeo containing Id2 cDNAs in the antisense orientation. 32D.3 cells were grown in suspension and maintained at equivalent exponential growth phases by seeding at 1×10$^5$ cells per ml culture medium. All subsequent analyses were performed using cells harvested at 0.5–1×10$^6$ cells per ml.

To prepare a recombinant expression construct encoding Id2 which could be regulated by the addition of tetracycline to the culture media, the Kpn1/HindIII filled-in fragment of Id2 cDNA was inserted into the pUHD 10-3 vector (26) at EcoRI blunt-ended sites to prepare a tTA-responsive Id2 expression vector. DNA from pUHD-10–3Id2 was used in addition to DNA from pTet-TAk (GIBCO), encoding the tetracycline-regulatable tTA protein. Stable transfectants were prepared in the U20S osteosarcoma cell line by performing a 3 vector transfection using LipofectAmine (GIBCO) at a DNA ratio of 5:5:1 between pTet-Id2:ptet-TAk:pcDNA-3 and selected in the presence of DME/10%FBS/G418 (0.6 mg/ml)/tetracycline (5 μg/ml) media was changed after 2 days. A parallel transfection in which pU/BID10-3Id2 DNA was replaced by a comparable pU/BID10-3-derived recombinant plasmid containing a cDNA encoding luciferase was used to prepare control cell lines. To show expression of Id2, cells were trypsinized and plated with varying concentrations of tetracycline (0–1000 ng/ml).

RNA preparation and Northern Blot Analysis. Total RNA was extracted from exponentially growing 32D.3 myeloid progenitor cells or from these cells deprived of IL-3 and analyzed by Northern blot hybridization. 20 μg of total RNA were fractionated by electrophoresis in 1% agarose-formaldehyde gels, blotted and hybridized to full-length cDNAs of mouse Id1 a, Id2, Id3, and Id4 and a 192-bp fragment of Id1b cDNA that uniquely recognizes Id1b (a region corresponding to amino acids 135–168 and 3' untranslated sequences). The cDNAs were radiolabelled with [$^{32}$P]dCTP by random priming (Amersham Corporation). Membranes were washed as previously described (12) and exposed for autoradiography.

Expression of Id genes and immunoblot analysis. Id gene expression was induced by addition of 1 μM dexamethasone (Sigma) for 16 hours. Cells were then collected at the indicated times by centrifugation, washed in PBS, and whole cell lysates were prepared by resuspending the pellets in RIPA buffer (150 mM NaCl, 1 mM EDTA, 1% Nonidet P-40, 1% sodium deoxycholate, 20 mM Tris-HCl pH 7.2) containing protease inhibitors (1 μM phenylmethyl-sulfonylfluoride, 0.01 μM benzamidine HCl, 1 μg/ml o-phenanthroline, and 0.5 μg/ml each of antipain, leupeptin, pepstatin A, and aprotinin). The lysates were then clarified by centrifugation and examined by 12.5% SDS-PAGE. Western blot analysis was carried out to detect expression of Id proteins using the sc-489 rabbit polyclonal antibody against Id2 (Santa Cruz Biotechnology, Santa Cruz, Calif.) and rabbit polyclonal antibodies generated against bacterially expressed Id1 or Id3 (C. Hernandez, unpublished). The expression of Bax proteins was monitored using a rabbit anti-Bax polyclonal sc-930 (Santa Cruz Biotechnology, Santa Cruz, Calif.). Briefly, blots were washed with blocking buffer [4% milk powder and 0.2% Tween-20 in phosphate-buffered saline (PBS)], incubated with anti-Id2 or Bax antibodies (used at a 1:1000 dilution in blocking buffer), washed, and incubated with peroxidase-conjugated rabbit IgG. The blots were washed again and developed by use of the ECL system (DuPont).

Viability and apoptosis assays. To investigate the effects of Id gene expression upon viability, cells growing exponentially in the presence of IL-3 (20 U/ml) were treated with dexamethasone for 16 hours. The cells were collected by centrifugation at 200×g for 10 min, washed twice in PBS, and resuspended in RPMI medium with 10% fetal bovine serum without IL-3. The number of viable cells was determined at various times after IL-3 withdrawal by trypan blue dye exclusion. After cytospin, DNA fragmentation was visualized following incorporation of digoxigenin-labeled oligonucleotides [mediated by terminal deoxynucleotidyl transferase (65)] using the Apotag TUNEL (terminal deoxynucleotidyl transferase mediated dUTP nick end labeling) assay kit (Oncor).

To determine the extent of apoptosis in U20S cells transfected with pTet-Id2 DNA, cells were plated at a density of $5 \times 10^5$ cells per p100 plate and allowed to adhere for 24 hours in the presence of 1000 ng/ml tetracycline (tet). Then the media was changed to either 0 or 1000 ng/ml tet after 2 washes with PBS. The cells were maintained in the culture for 4 days before harvesting by trypsinization (floating cells were also harvested). These cells were washed in PBS, fixed with 70% EtOH at 4° C. for a minimum of 1 hour, washed with PBS and stained with PBS/RNase (50 μg/ml)/propidium iodide (25 μg/ml). DNA content was determined by flow cytometry on a FACSort (53).

Using the materials and methods described above, we determined the levels of Id1a, Id1b and Id2 mRNA in 32D.3 cells are differentially regulated by IL-3. To assess the potential role of Id family proteins in myeloid cell apoptosis, we examined Id gene expression in 32D.3 myeloid progenitor cells before and following the removal of L-3, a cytokine required for the survival of these cells in culture (3, 62). Northern blot analysis revealed a large decrease in the level of Id1a mRNA after 8 hours of IL-3 withdrawal whereas there was a detectable increase in the level of Id2 transcripts. Id3 and Id4 expression were not detected in these cells, although Id1b, which is expressed in 32D.3 cells, did not change over the course of these experiments. Id1a and Id2 protein levels were analyzed by Western blot analysis at these same time points after IL-3 withdrawal, and we observed changes that paralleled those occurring at the RNA level. The observation that Id gene expression is regulated during survival factor withdrawal raised the possibility that Id1a and Id2 may be regulators of the apoptotic response of 32D.3 cells to IL-3 deprivation.

Id2 enhances apoptosis in 32D.3 myeloid cells following IL-3 withdrawal. Since Id2 levels in 32D.3 cells increased in association with IL-3 withdrawal, we examined the effect of increasing Id2 expression on the apoptotic response of these cells. 32D.3 myeloid progenitor cells were transfected with the dexamethasone (dex)-inducible pMAMNeo expression vector containing a full-length Id2 cDNA. The expression of Id2 in clones and pools of transfectants was determined in immunoblots, and we observed a 3–4 fold increase in Id2 protein levels upon treatment of the cells with dex for 16 hours as compared to cells transfected with vector DNA or with a pMAMNeo recombinant plasmid with Id2 in the antisense orientation. When examined for the extent of apoptosis by the TUNEL assay following IL-3 withdrawal (Gavrieli et al. 1992), both Id2 transfected clones and pools of clones exhibited significantly elevated apoptosis relative to what was observed in vector-only or Id2 antisense transfectants. To further confirm that these changes were due to increased apoptosis, we examined these same cell lines by FACS analysis following IL-3 removal and observed that the subdiploid population, indicative of apoptotic DNA fragmentation, was significantly augmented in each of the cell lines expressing high levels of Id2 compared to control cells.

To extend our assessment of the effects of Id2 gene expression on the rates of myeloid cell death, we examined these transfectants by trypan blue dye exclusion for evidence of cell death when grown under optimal conditions and at various times following IL-3 withdrawal. Constitutive expression of Id2 had only minor effects on viability in the presence of IL-3, during the 16 hours of treatment with dex. Following the withdrawal of IL-3, however, we observed dramatically accelerated rates of death relative to control cells. These rates were comparable to those documented in IL-3-deprived 32D.3 cells ectopically expressing E2F-1 and c-myc, both of which are potent inducers of apoptosis (3, 31). The morphology of cells taking up dye in both the control and transfected cultures was characterized by a shrunken cytoplasm, condensed chromatin and the presence of apoptotic bodies indicating that all these cells had died an apoptotic cell death. Therefore, enforced expression of Id2 exacerbates the rate of apoptotic death of 32D.3 myeloid cells following IL-3 withdrawal. We then examined more closely whether enforced Id2 expression could compromise 32D.3 cell survival in the presence of IL-3. The various cellular transfectants were examined after three days of induction of Id expression with dex in the presence of IL-3. Approximately 10–15% of the cells in each of the cultures exhibited nuclear fragmentation characteristic of apoptotic cells. These data indicate that IL-3 is able to effectively antagonize the pro-apoptotic effects of Id2.

Id2-induced apoptosis of 32D.3 cells and U20S osteosarcoma cells is concentration-dependent. To examine more closely the association between enhanced Id2 expression and the increased rate of cell death upon IL-3 withdrawal from 32D.3 cells, we obtained transfected clones of 32D.3 cells expressing varying levels of Id2 protein (clones 2, 3, 4 and an a pool of Id2 transfectants). These cells were subjected to IL-3 deprivation and analyzed for cell death by the TUNEL assay 16 hours after IL-3 withdrawal. The Id2 pool of transfectants and clone 3 exhibited the highest rate of cell death and also express the highest levels of Id2 protein. Lower levels of Id protein were correlated with less apoptosis. Interestingly, even a very small increase in the intracellular concentration of Id2 increased the extent of apoptosis as compared with vector-transfected cells. Using Pearson's Correlation Coefficient we related the percentage of apoptotic cells to Id2 levels of expression in the different transfectants determined by densitometry and obtained an R value of 0.98, indicating a close correlation between Id2 expression and the degree of apoptosis. These results indicate that Id2-induced apoptosis is concentration-dependent.

To further examine the effects of Id2 on apoptosis in a different cell type, we used the osteosarcoma U20S cell line. Stable transfectants were prepared in which the level of Id2 expressed from a recombinant expression vector could be regulated by tetracycline. Transfected cultures of tet-regulatable luciferase were also examined as controls. We examined different clones of transfected cells for Id2 expression following treatment with various concentrations of tetracycline (0–1000 ng/ml) in the culture media. To determine whether cells underwent apoptosis when Id2 levels were raised, we measured the DNA content of the cells four days after tetracycline (1000 ng/ml) was removed from the media. The results demonstrate a large proportion of apoptotic cells with subdiploid DNA content in cultures of U20S clone 9 cells following removal of tetracycline and the consequent induction of Id2 expression. This effect was not observed in control cells transfected with tetluciferase and grown in the presence or absence of tetracycline. Therefore, the pro-apoptotic activity of Id2 is observed in other cell types and appears to be dose-dependent. Interestingly, a low level of exogenous Id2 seems to be well-tolerated by U20S cells (34), but expression at higher levels, such as those observed in this experiment, leads to apoptosis. Furthermore, the observation that Id2 overexpression can promote apoptosis in U20S cells in the presence of serum indicates that high levels of Id2 can override the protective effects of survival factors utilized by these tumor cells.

Different members of the Id gene family have distinct apoptotic activities in 32D.3 myeloid cells. Having observed that Id2 promotes cell death, we examined whether other members of the Id gene family had similar activities. We prepared stable transfectants of 32D.3 cells expressing Id1a and Id3 in pMAMNeo. In the presence of dex, both Id1a and Id3 proteins were elevated to 3–4 fold higher levels than those observed in comparable cells transfected with vector DNA and selected in neomycin. Apoptosis and the rate of cell death in these transfectants were examined as before. While Id1a had a detectable activity in augmenting the rate of cell death, expression of Id3 was without effect. Therefore, in 32D.3 myeloid cells Id proteins are not functionally equivalent. Furthermore, although Id1a overexpression can augment apoptosis, its decreased expression following IL-3 withdrawal indicates it may not play a physiologic role in the programmed cell death of this particular cell type. In contrast, Id2 expression is increased following EL-3 withdrawal, an observation which is consistent with its role in promoting apoptosis.

Helix-loop-helix mediated dimerization of Id2 is not required for Id2-enhanced apoptosis. Id genes heterodimerize with bHLH transcription factors blocking the formation of bHLH protein dimers required for DNA binding and transcriptional activation (40, 48). Since the HLH domains through which dimerization is mediated are highly conserved in all known members of the Id gene family, our finding that Id1 a and Id2, but not Id3, enhanced apoptosis of 32D.3 cells was unexpected. We therefore sought to determine which regions of Id2 were required for this biologic activity. Recombinant expression plasmids were prepared in pMAMNeo containing cDNAs encoding Id2 proteins harboring deletions of either the N-terminal region (pId2ΔN-ter), the C-terminal region (pId2ΔC-ter), or the BLH region (pId2ΔHLH). These plasmids were transfected into 32D.3 cells, and pools of clones and individual clones were examined for expression of these altered Id2 proteins following 16 hours of treatment with dex. In the pId2ΔN-ter transfectant pool we observed levels of expression slightly higher than those observed in cells expressing transfected full-length Id2. The Id2ΔHLH mutant was also detected by immunoblotting but, as before, was present at low levels. We could not detect the Id2ΔC-ter protein in immunoblots despite examination with several different antibodies, and we interpret this result to indicate that the Id2ΔC-ter mutant protein is unstable, although it exists in sufficient quantities to promote cell death. Deletion of the C-terminal portion of Id3 has been reported previously to render this protein unstable (8).

When these pools of transfectants were examined for apoptosis following IL-3 withdrawal, we observed the expected enhancement in apoptosis in cells expressing exogenous Id2, and a similar level of apoptosis was also observed in cells expressing the pId2ΔC-ter encoded protein. Surprisingly, cell cultures transfected with the Id2 mutant lacking the HLH domain exhibited much higher rates of cell death than those observed in the wild-type Id2 transfectants, despite the fact that these cells expressed lower levels of exogenous Id2 protein. This increased activity was observed in several independent transfectants. Deletion of the HLH domain renders the Id2 protein less stable, yet even low levels of this molecule promote high levels of apoptosis in myeloid progenitors. In contrast, cells expressing the pId2ΔAN-ter encoded protein did not exhibit enhanced apoptosis, despite the easily detectable levels of endogenous Id2 protein seen in pools and several clones of Id2ΔN-ter transfectants. To extend this assessment, we examined the rates of cell death of these transfectants by trypan blue dye exclusion following IL-3 withdrawal. Rates of cell death following IL-3 /withdrawal of these clones paralleled closely the pattern of TUNEL-positive cells. Therefore, Id2 enhancement of apoptosis requires its N-terminal region, but does not require HLH mediated functions.

Id2-induced apoptosis is associated with the expression of Bax. We surveyed the expression of several known regulators of apoptosis in an effort to identify candidate mediators of Id2-induced apoptosis of 32D.3 myeloid cells. In Id2 transfectants cultured in IL-3, we observed an elevated steady state level of the pro-apoptotic bcl-2 family member Bax, but no changes of other known regulators including Bad, Bcl-2, Bcl-$X_L$ and Bcl-$X_S$. Bax levels were elevated in cells expressing either Id2 or Id2ΔBLH, relative to 32D.3 cells transfected with the vector DNA alone, DNA from the same vector containing Id2 in the antisense orientation, or DNA from Id2ΔN-ter. In each case, we examined the expression of Id2 proteins in lysates of these same cells. These pools of transfectants generally expressed comparable levels of Id2 wild-type and mutant proteins, although the Id2ΔHLH mutant was present at lower levels.

To further assess the role of Id2 as a regulator of Bax, we examined a pool and an independent clone (clone 5) of 32D.3 cells stably transfected with antisense Id2 cDNA constructs. Cultures of these transfectants were examined by Western blot analysis following 24 hours of dex treatment in the presence of IL-3. Induced antisense expression by treatment with dex decreased levels of Id2 and Bax, whereas no changes in Bax levels were observed in vector transfected cells treated with dex.

Our finding that it was possible to decrease the levels of endogenous Id2 following expression of antisense Id2 RNA provided an opportunity to examine this effect on the viability of 32D.3 cells following IL-3 withdrawal. As shown in Table 3, we detected a significantly increased survival over the entire course of IL-3 withdrawal in both the antisense Id2 expressing pool of cells and clone 5 cells. Taken together, these results indicate that modulating Id2 levels leads to parallel changes in Bax levels, and these correlate with Id2-induced apoptosis.

TABLE 3

Change in the percent survival following dex induction of antisense Id2*

| Time following | Transfectant | | |
|---|---|---|---|
| IL3 withdrawal | 32D.3 vector | antisense Id2c.5 | antisense 1d2 pool |
| 1 hr | 1.0 | −4.0 | 1.0 |
| 16 hr | 4.1 | 26.6 | 40.6 |
| 19 hr | 4.4 | 40.0 | 37.2 |
| 22 hr | 6.8 | 29.0 | 33.3 |

* These values are the difference in percent survival of cells in the absence and presence of antisense Id2 induction of each transfectant following treatment with dexamethasone as determined by trypan blue dye exclusion. These values are from a single experiment and are representative of three independent experiments.

A major biological challenge throughout development is the coordination of cellular proliferation and death. Apoptosis is a form of regulated cell death required throughout development for the maintenance of tissue homeostasis. Genes that regulate the initiation or execution of apoptotic cell death have been identified (for review see 70), and among these are some which participate in other important cellular processes as well. We have identified a role for Id2, a known modulator of both differentiation and cell proliferation, in the regulation of apoptosis. Nonetheless, some tumor cell lines can tolerate high levels of Id2 protein (2, 16, 75), and it is possible that such cell lines have undergone selection for changes that suppress Id-mediated apoptosis.

The observation that Id2 mediates both cellular proliferation and apoptosis is consistent with work identifying other multifunctional proteins as gatekeepers of the $G_1/S$ transition. Two important molecular features of the mechanisms utilized by Id genes to promote entry into S-phase have been described: 1) Id2 can bind to members of the Rb tumor suppressor family and overcome their growth inhibition and 2) Id1 can antagonize the bHLH mediated activation of a known inhibitor of cell cycle progression, p2/WAF1 (34, 45, 59). These observations are most compatible with a model of Id function which proposes that during the $G_1$ to S transition Id proteins are released from binding partners such as Rb and then become available to inhibit bHLH transcription factor-mediated gene expression (34). Regulation of Id activity at this juncture of the cell cycle might be further mediated by post-translational modifications such as phosphorylation (29). Previous studies of c-Myc, E2F-1 and p53 have suggested that the proliferative and apoptotic activities of these molecules are both likely to be associated with the ability to effect transcription, yet their effects on cell death and proliferation are dissociable events (9, 30, 33, 54, 58, 63, 64). Activation of either the proliferative or apoptotic pathway may thus result from differential transcriptional regulation of distinct sets of target genes (23, 33, 58, 63, 71). Our data indicate that the effects of Id2 on apoptosis and proliferation are also separable, since the HLH region is dispensable for the apoptotic function of Id2 but is required for all other known activities of Id2, contrary to the current view that bHLH factors or members of the Rb gene family are obligatory partners for Id gene functions.

Several models whereby Id2 functions to integrate signals mediating different biologic activities can be envisioned. Our observations that the N-terminal region of Id2 is required for its apoptotic activity and that the level of expression of a pro-apoptotic molecule, Bax, is closely correlated with the level of Id2 expression, raise the possibility that Id2 may be capable of influencing gene expression through an activity of its N-terminal domain. In such a model, Id2 might act in trans to either transcriptionally activate bona fide cell death genes or repress genes important for survival. In a related scenario, Id2 protein may sequester transcriptional regulators of survival genes or of apoptotic genes such as Bax. Our finding that deletion of the Id2 HLH domain increases the rate of apoptotic death by Id2 indicates that inhibition of Id function may be mediated by heterodimerization with Rb family members and bHLH proteins, which require the Id2 HLH domain for binding. Such a possibility is supported by the well-documented role of Rb in the inhibition of apoptosis (27, 49, 74), and the finding that bHLH transcription factors can also inhibit apoptosis (14). The observation indicating that Id gene expression is high in replicating cells and low in most well-differentiated tissues (4, 11, 16, 42) is consistent with this model and predicts that the dynamic balance between Id2 and its binding partners such as E47 or Rb influences whether a cell dies, proliferates or differentiates.

It has been previously demonstrated that Id genes are detectable in both the cytoplasm and nucleus (5, 34), and E47, a bHLH protein, has been shown to function as a nuclear chaperone for Id1 and Id3 (16). Id genes lack a nuclear localization signal and translocation of Id genes to the nucleus is thought to be mediated by HLH-mediated binding of Id genes to bHLH proteins. Id2ΔHLH enhances apoptosis and is likely to be localized exclusively in the cytoplasm. Our observation that the apoptotic function of Id2 does not require the HLH region implies that the apoptotic targets of the N-terminal domain of Id molecules may also be cytoplasmic. Such targets could be apoptotic effectors such as the Bax protein itself or, more likely, molecules that regulate the expression of genes important for apoptosis, such as BAX. In such a model, bHLH molecules or pRb present in the cytoplasm may still have an inhibitory effect on Id function, as might the transport of Id2 into the nucleus.

These models are not entirely exclusive of one another, and both invoke an apoptotic function for the N-terminal domain of Id2. There are 35 amino acids in Id2 which are 5' to the HLH domain and among these are the 32 amino acids deleted in pId2Δ-Nter. It is noteworthy that two Id2 loci have been described in the human genome, Id2A and Id2B (44). While Id2A encodes a polypeptide of 134 amino acids, Id2, Id2B encodes a 36 amino acid peptide which corresponds to the first 36 amino acids of Id2. While the identification of a cDNA encoded by Id2B containing an in-frame stop codon has been interpreted as suggesting that Id2B may be a transcribed pseudogene (44), our data indicate that Id2B encodes a novel Id2 related peptide. Other Id gene family members do not include comparable loci encoding shortened Id polypeptides, and under some circumstances Id proteins are processed to yield such a peptide and a residual protein of approximately 100 amino acids. This is consistant with our observation in murine cells of a second Id2 immunoreactive species which is slightly smaller than the full-length 14 kD Id2.

We observed that three different Id transcripts, Id1a, Id1b, and Id2 are expressed at detectable levels in 32D.3 myeloid cells, yet only Id1a and Id2 are regulated during apoptosis following IL-3 withdrawal. In contrast to Id2 and Id1 a, Id3 does not augment the apoptotic program in 32D.3 myeloid cells deprived of IL-3. Hence, our data indicate that all Id homologues are not equally active in inducing apoptosis in some cell types, and that each Id gene family member mediates different activities in different cell types. This conclusion is in concert not only with previous work demonstrating, that the ability of different Id genes to enhance proliferation is regulated by different cellular mechanisms (34), but also with the observation that there is little sequence similarity among Id homologues outside of their HLH domains (see e.g. 75). Id proteins are widely-expressed throughout development, and multiple Id genes are expressed in various tissues (35, 37, 39, 46, 61, 75). Our findings indicate that the Id gene family functions not only to promote cellular proliferation and inhibit differentiation, but also to coordinate tissue maturation by promoting apoptosis.

By binding to different classes of partners, different functional domains within the different Id molecules may be responsible for mediating distinct cellular activities. Given the variety of cellular processes that Id genes participate in and the number of signals to which they can respond (4, 6, 11, 16), we conclude that Id genes participate in the integration of these signals by activating and inactivating genes important for different cell fates including proliferation, differentiation, apoptosis and possibly, malignant transformation. Consistantly, an important role during development has already been defined for the emc gene of Drosophila (15), a functional homologue of Id which antagonizes the bHLH factors encoded by Daughterless and achaete-scute (20, 24).

Protocol for high throughput human apoptotic Id2 peptide binding assay

A. Reagents

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{32}$P human Id2 peptide 10x stock: $10^{-8}$–$10^{-6}$M "cold" human apoptotic Id2 peptide supplemented with 200,000–250,000 cpm of labeled apoptotic Id2 peptide (Beckman counter). Place in the 4° C. microfridge during screening.

Protease inhibitor cocktail (1000X: 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

Binding target: $10^{-7}$–$10^{-4}$M biotinylated EH47 HLH protein binding target (Kreider, B., R. Benezra, G. Rovera, and T. Kadesch. 1992. Science 255:1700–1702) in PBS.

B. Preparation of Assay Plates

Coat with 120 $\mu$l of stock N-Avidin per well overnight at 4° C.

Wash 2 times with 200 $\mu$l PBS.

Block with 150 $\mu$l of blocking buffer.

Wash 2 times with 200 $\mu$l PBS.

C. Assay

Add 40 $\mu$l assay buffer/well.

Add 10 $\mu$l compound or extract.

Add 10 $\mu l^{33}$P-Id2 peptide (20–25,000 cpm/0.1–10 pmoles/well=$10^{-9}$–$10^{-6}$M fin conc).

Shake at 25° C. for 15 minutes.

Incubate additional 45 minutes at 25° C.

Add 40 $\mu$l biotinylated EH47 (0.1–1 0 pmoles/40 $\mu$l in assay buffer)

Incubate 1 hour at room temperature.

Stop the reaction by washing 4 times with 200 $\mu$l PBS.

Add 150 $\mu$l scintillation cocktail.

Count in Topcount.

D. Controls For All Assays (Located on Each Plate)

a. Non-specific binding b. Soluble (non-biotinylated apoptotic Id2 peptide) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for modulating apoptosis of an isolated target cell having an undesirable level of apoptotic induction, the method comprising the steps of introducing into the cell a nucleic acid encoding a polypeptide comprising an N-terminal domain of a natural Id protein, said natural Id protein comprising an HLH domain and said N-terminal domain consisting of all residues N-terminal to said HLH domain, or a fragment of said N-terminal domain sufficient to modulate apoptosis in the cell, under conditions whereby the nucleic acid is expressed in the cell and apoptosis of the cell is modulated, and confirming the modulation of apoptosis of the cell, wherein said polypeptide does not have a functional Id HLH domain and the apoptosis modulation of the cell is independent of the ability of the polypeptide to form dimers via HLH-HLH interactions.

2. A method according to claim 1, wherein the polypeptide further comprises a non-Id peptide.

3. A method according to claim 1, wherein the polypeptide comprises fewer than 20 consecutive residues of the C-terminal 35 residues of the natural Id protein.

4. A method according to claim 1, wherein the natural Id protein is selected from Id1, Id2, Id3 and Id4.

5. A method according to claim 1, wherein the natural Id protein is Id2.

6. A method according to claim 1, wherein the polypeptide comprises an N-terminal domain of the natural Id protein.

7. A method according to claim 1, wherein the natural Id protein is selected from Id1, Id2, Id3 and Id4, and the polypeptide comprises an N-terminal domain of the natural Id protein.

8. A method according to claim 1, wherein the natural Id protein is Id2 and the polypeptide comprises an N-terminal domain of the natural Id protein.

9. A method according to claim 8, wherein the polypeptide further comprises a non-Id peptide.

10. A method according to claim 8, wherein the polypeptide comprises fewer than 20 consecutive residues of the C-terminal 35 residues of the natural Id protein.

11. A method according to claim 1, wherein the fragment comprises a sequence selected from the group consisting of residues 1–8 of any one of SEQ ID NOS:01–12; residues 27–40 of SEQ ID NO:1; residues 11–24 of SEQ ID NO:2; residues 13–26 of SEQ ID NO:3; residues 24–37 of SEQ ID NO:4; residues 16–29 of SEQ ID NO:5; residues 20–33 of SEQ ID NO:6; residues 14–27 of SEQ ID NO:7; residues 11–24 of SEQ ID NO:8; residues 11–24 of SEQ ID NO:9; residues 11–24 of SEQ ID NO:10; residues 11–24 of SEQ ID NO:11; and residues 11–24 of SEQ ID NO:12.

12. A method according to claim 11, wherein the polypeptide further comprises a non-Id peptide.

13. A method according to claim 11, wherein the polypeptide comprises fewer than 20 consecutive residues of the C-terminal 35 residues of the natural Id protein.

14. A method for modulating apoptosis of an isolated target cell, the method comprising the steps of:

generating a mutant of a polypeptide comprising an N-terminal domain of a natural Id protein, said natural Id protein comprising an HLH domain and said N-terminal domain consisting of all residues N-terminal to said HLH domain, or a fragment of said N-terminal domain sufficient to modulate apoptosis in the cell wherein said polypeptide does not have a functional Id HLH domain and the apoptosis modulation of the cell is independent of the ability of the polypeptide to form dimers via HLH-HLH interactions and wherein the peptide, when expressed in a susceptible cell, is capable of modulating apoptosis of the cell;

introducing the mutant into the cell, under conditions whereby the mutant modulates apoptosis of the cell; and confirming the modulation of apoptosis of the cell.

15. A method for modulating apoptosis of an isolated target cell having an undesirable level of apoptotic induction, the method comprising the steps of introducing into the cell a nucleic acid encoding a polypeptide comprising an N-terminal domain of a natural Id protein, said natural Id protein comprising an HLH domain and said N-terminal domain consisting of all residues N-terminal to said HLH domain, or recombined fragments of said N-terminal domain sufficient to modulate apoptosis in the cell, under conditions whereby the nucleic acid is expressed in the cell and apoptosis of the cell is modulated, and confirming the modulation of apoptosis of the cell, wherein said polypeptide does not have a functional Id HLH domain and the apoptosis modulation of the cell is independent of the ability of the polypeptide to form dimers via HLH-HLH interactions, wherein the recombined fragments comprise at least a first peptide comprising residues 1–8 of at least one of a sequence selected from the group consisting of SEQ ID NOS:01–12 and a second peptide comprising at least one of a sequence selected from the group consisting of residues 2740 of SEQ ID NO:1; residues 11–24 of SEQ ID NO:2; residues 13–26 of SEQ ID NO:3; residues 24–37 of SEQ ID NO:4; residues 16–29 of SEQ ID NO:5; residues 20–33 of SEQ ID NO:6; residues 14–27 of SEQ ID NO:7; residues 11–24 of SEQ ID NO:8; residues 11–24 of SEQ ID NO:9; residues 11–24 of SEQ ID NO:10, residues 11–24 of SEQ ID NO:11; and residues 11–24 of SEQ ID NO:12.

16. A method for modulating apoptosis of an isolated target cell comprising upregulating the expression of a transgene encoding a polypeptide comprising an N-terminal domain of a natural Id protein, said natural Id protein comprising an HLH domain and said N-terminal domain consisting of all residues N-terminal to said HLH domain, or a fragment of said N-terminal domain sufficient to modulate apoptosis in the cell, under conditions whereby apoptosis of the cell is modulated, and confirming the modulation of apoptosis of the cell, wherein said polypeptide does not have a functional Id HLH domain and the apoptosis modulation of the cell is independent of the ability of the polypeptide to form dimers via HLH-HLH interactions, wherein the fragment comprises a sequence selected from the group consisting of residues 1–8 of any one of SEQ ID NOS:01–12. residues 27–40 of SEQ ID NO:1; residues 11–24 of SEQ ID NO:2; residues 13–26 of SEQ ID NO:3; residues 24–37 of SEQ ID NO:4; residues 16–29 of SEQ ID NO:5; residues 20–33 of SEQ ID NO:6; residues 14–27 of SEQ ID NO:7; residues 11–24 of SEQ ID NO:8; residues 11–24 of SEQ ID NO:9; residues 11–24 of SEQ ID NO:10; residues 11–24 of SEQ ID NO11; and residues 11–24 of SEQ ID NO: 12.

17. A method for modulating apoptosis of an isolated target call comprising upregulating the expression of a transgene encoding a polypeptide comprising an N-terminal domain of a natural Id protein, said natural Id protein comprising an HLH domain and said N-terminal domain consisting of all residues N-terminal to said HLH domain, or a fragment of said N-terminal domain sufficient to modulate apoptosis in the cell, under conditions whereby apoptosis of the cell is modulated, and confirming the modulation of apoptosis of the cell wherein said polypeptide does not have a functional Id HLH domain and the adoptosis modulation of the cell is independent of the ability of the polypeptide to form dimers via HLH-HLH interactions.

18. A method for modulating apoptosis of an isolated target cell comprising upregulating the expression of a transgene encoding a polypeptide comprising an N-terminal domain of a natural Id protein, said natural Id protein comprising an HLH domain and said N-terminal domain consisting of all residues N-terminal to said HLH domain, or a fragment of said N-terminal domain sufficient to modulate apoptosis in the cell, under conditions whereby apoptosis of the cell is modulated, and confirming the modulation of apoptosis of the cell, wherein said polypeptide does not have a functional Id HLH domain and the apoptosis modulation of the cell is independent of the ability of the polypeptide to form dimers via HLH-HLH interactions wherein the natural Id protein is Id2 and the polypeptide comprises an N-terminal domain of the natural Id protein.

19. A method for modulating apoptosis of at isolated target cell comprising upregulating the expression of a transgene encoding a polypeptide comprising an N-terminal domain of a natural Id protein, said natural Id protein comprising an HLH domain and said N-terminal domain consisting of all residues N-terminal to said HLH domain, or recombined fragments of said N-terminal domain sufficient to modulate apoptosis in the cell, under conditions whereby apoptosis of the cell is modulated, and confirming the modulation of apoptosis of the cell, wherein said polypeptide does not have a functional Id HLH domain and the apoptosis modulation of the cell is independent of the ability of the polypeptide to form dimers via HLH-HLH interactions, wherein the recombined fragments comprise at least a first peptide comprising residues 1–8 of any one of a sequence selected from the group consisting of SEQ ID NOS:01–12 and a second peptide comprising any one of a sequence selected from the group consisting of residues 27–40 of SEQ ID NO:1; residues 11–24 of SEQ ID NO:2; residues 13–26 of SEQ ID NO:3; residues 24–37 of SEQ ID NO:4; residues 16–29 of SEQ ID NO:5; residues 20–33 of SEQ ID NO:6; residues 14–27 of SEQ ID NO:7; residues 11–24 of SEQ ID NO:8; residues 11–24 of SEQ ID NO:9; residues 11–24 of SEQ ID NO:10; residues 11–24 of SEQ ID NO:11; and residues 11–24 of SEQ ID NO:12.

20. A method of identifying an agent active at the level of apoptotic Id polypeptide cellular function comprising the steps of:

modulating apoptosis of an isolated target cell according to the method of claim 1;

contacting the cell with an agent; and determining whether the agent further modulates apoptosis in the cell.

21. A method of identifying an agent active at the level of apoptotic Id polypetide cellular function comprising the steps of:

modulating apoptosis of an isolated target cell according to the method of claim 8:

contacting the cell with an agent; and determining whether the agent further modulates apoptosis in the cell.

22. A method of identifying an agent active at the level of apoptotic Id polypeptide cellular function comprising the steps of:

modulating apoptosis of an isolated target cell according to the method of claim 10;

contacting the cell with an agent; and determining whether the agent further modulates apoptosis in the cell, wherein the polypeptide further comprises a non-Id peptide.

* * * * *